Figure 1:
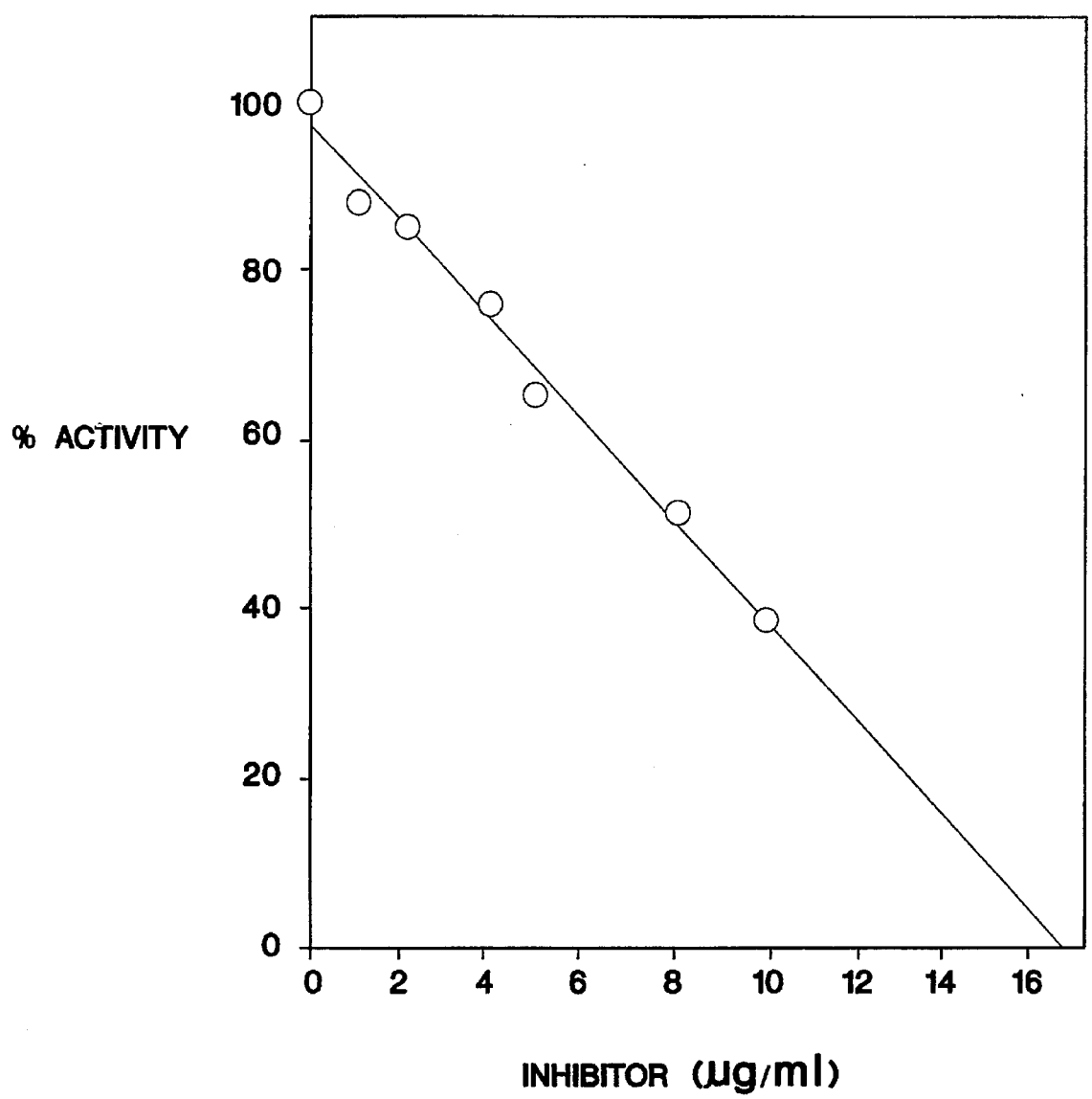

United States Patent [19]

Vu Khue et al.

[11] Patent Number: 5,624,831
[45] Date of Patent: Apr. 29, 1997

[54] IMMOBILIZED ACETYLCHOLINESTERASE STABILIZED BY A FILM OF GELATIN OR ALBUMIN CONTAINING TREHALOSE

[76] Inventors: Nguyen Vu Khue, 23 Rue du Paradis, Wittersheim, F-67670 Mommenheim; Phillippe Poindron, 14 Rue Andre Malraux, F-67400 Illkirch; Roland Maes, Bildhauerhof, 34, F-67190 Mutzig, all of France

[21] Appl. No.: 405,816

[22] Filed: Mar. 16, 1995

[30] Foreign Application Priority Data

Mar. 28, 1994 [BE] Belgium ............................. 09400331

[51] Int. Cl.⁶ ..................... C12N 11/02; C12N 11/14; C12N 11/08; C12Q 1/46
[52] U.S. Cl. ................. 435/177; 435/20; 435/176; 435/180
[58] Field of Search ..................... 435/19, 20, 176, 435/177, 180, 262.5

[56] References Cited

U.S. PATENT DOCUMENTS

| 4,324,858 | 4/1982 | Goodson et al. | 435/20 |
| 4,689,297 | 8/1987 | Good et al. | 435/174 |

FOREIGN PATENT DOCUMENTS 52-57390  5/1977  Japan.

*Primary Examiner*—David M. Naff
*Attorney, Agent, or Firm*—William J. Daniel

[57] ABSTRACT

Acetylcholinesterase and/or a receptor of acetylcholinesterase is immobilized on a solid support and stabilized by covering with a protective film of gelatin and/or albumin containing trehalose. The film is applied by covering the immobilized acetylcholinesterase and/or receptor of acetylcholinesterase with a layer of a gel-forming solution of gelatin or albumin in an evaporable solvent containing dissolved trehalose, and evaporating the solvent to leave the film. The film provides stability against dry heat, organic solvents, proteases and changes in pH. Other additives such as polyhydric alcohols, organic solvents, polymers and/or ionic and non-ionic components may be present to increase stabilization. A diagnostic kit or chromatography column may be formed containing the stabilized immobilized acetylcholinesterase and/or receptor of acetylcholinesterase.

4 Claims, 3 Drawing Sheets

IMMOBILIZED ACETYLCHOLINESTERASE STABILIZED BY A FILM OF GELATIN OR ALBUMIN CONTAINING TREHALOSE

OBJECT OF THE INVENTION

This invention concerns a solid support immobilizing acetylcholinesterase and/or a receptor of acetylcholinesterase stabilized, and its process of obtention

TECHNOLOGICAL BACKGROUND OF THIS INVENTION

Recent developments in molecular biology and biochemistry have allowed the use of numerous biologically active components in processes of synthesis, of separation and/or of diagnosis. Among these biologically active components, enzymes proved to be good catalysts due to their strong affinity for their substates and their vigorous catalyst activity functioning under mild conditions.

However, these processes often require a modification of temperature, pH, concentration of reagents, dessication of support, that are frequently at the cause of the denaturation or destruction of the enzymes used. Enzymes are characterized by a specific tridimensional conformation obtained through the arrangement of aminoacids and the bonds existing between these elements. Denaturation reactions induce minor or major modifications of this conformation without necessarily perturbing the aminoacid sequence of the denatured enzymes. This denaturation may result in a decrease or even the complete inactivation of the biological activity of the enzyme.

The acetylcholinesterase enzyme and the menbrane-bound receptor of acetylcholinesterase belong to the enzymes and enzymatic receptors whose spontaneous inactivation at room temperature is very fast. Yet, these two entities possess a great analytical and diagnosis potential for the detection of some kinds of pesticides, the evaluation of the blood level of certain drugs and the diagnostic of some diseases (muscular myastheny, Alzheimer disease, . . .).

Most currently used pesticides possess an inhibitory activity acting on a defined reaction site. Some pesticides, belonging to the group of the carbamates and of the organophosphors, inhibit cholinesterase, with the result that the transmission of the nervous influx is perturbated. The detection of pesticides traces contaminating food either for animal or for human consumption (wine, cereals, fruit juices, baby foods, salads etc . . .) is presently based on a technique of gaseous chromatography. This technique is highly sophisticated and performs well but is also difficult to apply, lengthy and costly. In addition, it does not allow a global i.e. broad determination of the pesticides potentially involved but analyzes the samples submitted for analysis directly in a detailed way for individual pesticides. A diagnostic tool sensitive enough and simple enough to be routinely applied for the detection in the environment of the group of pesticides perturbating nervous influxes by inhibiting cholinesterase is not yet available. The lack of stability of cholinesterase and of its receptor have led to detection kits designed to analyse the activity of the free enzyme (Sigma chemicals). The potential presence of inhibitory substances is inferred from the activity measured. Another approach to monitor the presence of pesticides involves antibodies against some classes of pesticides, which are applied in an enzyme-based immunological determination of these pesticides (Milllipore). These methods are not sensitive enough for the detection of drugs in the serum of treated patients: a diagnostic kit useful for the monitoring of drug levels in the serum of patients treated for myasthenis or Alzheimer disease is now in great demand but has not yet been developed.

PRESENT STATE OF THE TECHNIQUE

Various methods designed at stabilizing enzymes have been proposed for the reduction or the total prevention of their denaturation due to dessication, pH changes, organic solvents., proteases, pressure changes etc. Processes of stabilization of enzymes dissolved in an aqueous solution are well known (Enzyme stabilization. Gianfreda and Scarfi. Mol. Cell Biochemistry 1991, 110, 97–128). Among the described methods worth mentioning are immobilisation on a solid support, addition of protective agents, coupling to other components, reticulation by bifunctional (cross-linking) agents. Some solubilised enzymes are stabilized by sugars but, in general, sugars stabilize enzymes normally only under water freezing temperatures, preferably below $-20°$ C. or colder.

French patent claim FR-2677373 describes a detection kit for pesticides of the organophosphorus and/or carbamate families in aqueous solution, based on cholinesterase whose activity is determined by a well known colorimetric determination (A new and rapid colorimetric determination of acetylcholinesterase activity. Ellman et al. Biochem. Pharmacology 1961, 7, 88–95). The pesticide detection element of the kit is an enzyme of the cholinesterase family fixed according to a complex method to a solid support by the help of a proteinaceous matrix. The proteinaceous matrix is gelatin, in which the enzyme is dissolved, thereafter cross-linked or cross-linked by a bifunctional agent as glutaraldehyde. The solid support is a rod terminated by an helix and attached to a stopper, immersing in a test tube containing an aqueous medium consisting of 0.9% NaCl buffered at pH 7 by a primary and a secundary phosphate, and a bacteriostatic. This solution keeps constantly wet the enzyme attached in a covalent way to the solid support by the gelatin enrobing the rod and the helix. The helix-rod device is commercially available (Helix immunostick maxisorp NUNC).

The preparation of these helixes coated with gelatin containing and fixing the enzyme, requires that the helixes be maintained at $37°$ C. in an aqueous solution of 5% gelatin containing the enzyme, after which they are taken out of the gelatin solution and dried. The helixes are thereafter immersed in a bath of 1% glutaraldehyde and then rinced with distilled water. This process is followed by a bath in a solution of glycine to inactivate the glutaraldehyde, another rinse with distilled water and finally enclosure within a test tube containing an aqueous solution buffered at pH 7. Storage of the kits is preferentially at $4°$ C.

However, the availability of the supported enzyme in a dry form is advantageous for some applications such as diagnostic kits. It is known that some proteins immobilized on a solid support acquire a stabilization often superior to that observed when the same proteins are kept in a solubilized form. The immobilization of these proteins may be achieved by covalent fixation on the solid support, adsorptive interactions, capture of the protein within a gel, upon fibers or beads, coupling by bifunctional reagents and/or encapsulation in microcapsules.

The claim of patent WO 92/08134 describes the formation of gelatin beads enclosing magnetic particles, and which possess free reactive groups upon which it is possible to attach antibodies. These beads have the advantage to be easily used in liquid media for the separation of biological substances. Patent FR-2677373, above mentioned, relies on a similar technique of immobilisation.

Figure 2:
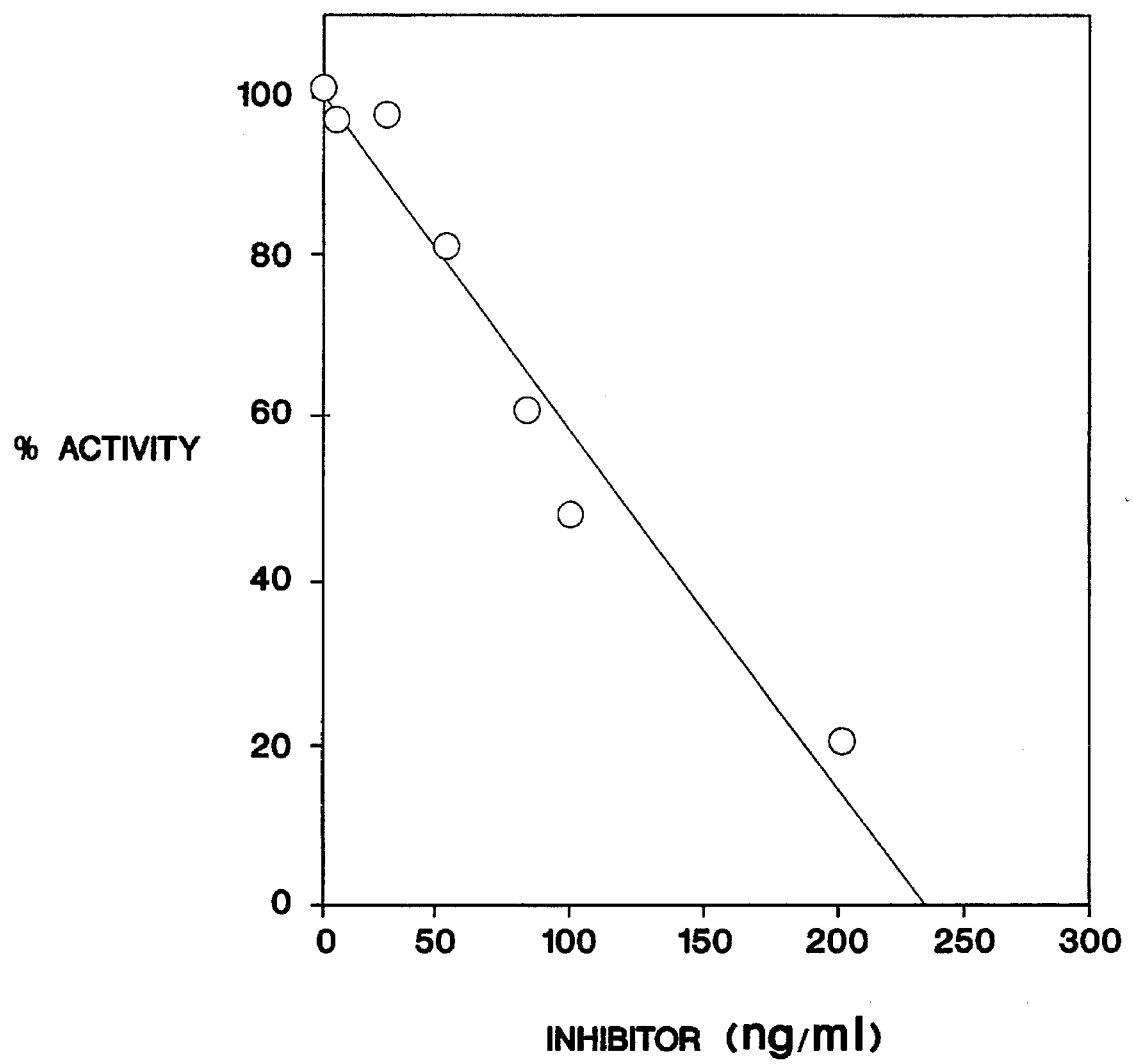

Patent application EP-140489 describes processes for stabilization of biological substances on a solid phase. These biological substances are characterized by an immunological activity and are chosen among the group composed of antibodies, antigens and haptens (hormones, globulins, viral antigens, vitamins, etc.). The process of stabilization of these substances immobilized on a solid phase entails the immersion of these immuno-active substances in a solution comprising sugars and proteins. The described sugars in that patent claim are ribose, glucose, fructose, mannose, galactose, maltose, lactose, sucrose, oligosaccharides or polysaccharides such as dextran and dextrin. Among the described proteins are mentioned bovine serum albumin, human albumin, sheep albumin and gelatin. However, this document neither describes nor mentions the stabilization of molecules presenting an enzymatic activity. Indeed , enzymes are characterized by an extraordinary lability. For example, acetylcholinesterase extracted from the torpedo fish looses normally all its enzymatic activity when kept dry at 4° C. for longer than 7 days.

U.S. Pat. No. 4,324,858 describes a detection kit for pesticides comprising a cholinesterase stabilized by a switterionic buffer and dried on a solid support of paper, under vacuum. Sugars are regularly used elsewhere in the prior art to stabilize dried enzymes.

It is also known that some sugars are excellent stabilizing agents for enzymes when these are dried at room temperature. It was recently found that trehalose (α-D glucopyranosyl-α-D-glucopyranoside) is an excellent stabilizing agent for enzymes dried at room temperature (Extraordinary stability of enzymes dried in trehalose. C. Colaco et al. Biotechnology 1992, 9, 1007–1013).

Patent application EP-A- 0192320 states that agents which are effective for protecting the immunologic activity of antibodies are not effective for enzymes. This document describes a process of stabilization of an enzyme conjugated to an antibody suspended in a protecting medium composed of a sugar and a protein. This document mentions that the enzyme is free, i.e. not immobilized on a solid support and that the most satisfactory results are observed with lactose and trehalose, and that 1% ovalbumin increases further the stability induced by the sugars.

However, the enzymes described in this document are the enzymes used in immuno-enzymatic tests, i.e. peroxidase, alkaline phosphatase, catalase and glucose oxidase. It is important to note that all enzymes are not the same and that a protection adequate to preserve the enzymatic activity of a phosphatase, a catalase or a peroxidase may not be satisfactory or sufficient for a very sensitive enzyme such as an esterase, in particular an acetylcholinesterase or the receptor of an esterase enzyme such as acetylcholinesterase.

PURPOSE OF THE INVENTION

The object of the present invention is a solid support immobilizing acetylcholinesterase and/or a receptor of cholinesterase, having improved stability.

A particular purpose of this invention is an improved stability against dry heat (dessication), against the activity of organic solvents, of proteases and change of pH.

Another purpose of the invention is to devise a process for producing such a support that is simple to execute, fast to carryout and cheap to produce.

PRINCIPAL CHARACTERISTICS OF THE INVENTION

The present invention concerns a solid phase immobilizing acetylcholinesterase and/or a receptor of acetylcholinesterase, covered by a protective film composed of gelatin and/or albumin and containing trehalose. By solid phase is understood any solid structure upon which a component with a biological activity may be immobilized by covalent bonds or adsorptive interactions. Such solid supports may be take the form of a chromatography column, wells of microtitration plates, beads, gels, fibers and/or any support made glass, plastic, metal, paper and/or any other material.

The protective film of gelatin and/or albumin is a tridimensional structure such as a gel in which a solvent is immobilized. This gel is thus composed of a tridimensional reticulum of macromolecules or particles connected in a continuous liquid phase. According to the invention, the film also contains trehalose.

Quite unexpectedly, it was found that the protective film according to the invention achieves a stabilization of cholinesterase and/or a receptor of cholinesterase against dessication, organic liquids, extremes of pH and the action of proteases.

By stabilisation is understood the maintenance of the enzymatic activity of the reaction site(s) of acetylcholinesterase or a receptor of acetylcholinesterase.

The protective film according to the invention is characterized by the inexpected synergistic effect of the protective action of gelatine (and/or albumin) and trehalose.

Other additives, as defined by Gray (Additives and enzyme stability. Biocatalyses 1, 187–196, 1988) and Gianfredda et al. (Enzyme stabilization. Mol. Cell Biochemistry 1991, 110, 97–128) may also be applied to increase this stabilization. These additives may be polyhydric alcohols, organic solvents, polymers and/or ionic or non-ionic components.

Advantageously, the stabilization of the solid support according to the invention is observed when said support is dried, for example when it is dessicated at elevated temperatures (preferably comprised between 4° C. and 37° C., even at temperatures close to 50° C.).

The present invention concerns also the chromatography column or the diagnostic kit comprising the solid support according to the present invention.

Another aspect of the present invention concerns the process for producing the solid support according to the present invention, in which one attaches acetylcholinesterase and/or a receptor of acetylcholinesterase on the solid support, one covers this solid phase with a gel, solution comprising gelatin and/or albumin as well as trehalose, and one creates on the said solid support a protective film by evaporation of the solvant of the gel.

Preferably, the concentration of the gelatin in the solution is comprised between 0.5 and 10 mg/ ml of solution, preferably comprised between 1 and 5 mg/ml of solution.

Preferably, the concentration of albumin in the solution is comprised between 5 and 100 mg/ml of solution, preferably comprised between 10 and 50 mg/ml of solution.

Advantageously, the concentration of trehalose in the solution is comprised between 10 and 150 mg/ml of solution, preferably comprised between 20 and 50 mg/ml of solution.

The present invention will be described in a more detailed manner through the following examples given to illustrate in a non-limitative way the present invention.

SHORT DESCRIPTION OF THE FIGURES

FIG. 1 represents the inhibition of the enzymatic activity of cholinesterase (in %), in relation to increasing doses of pyridostygmin in the serum.

FIG. 2 represents the inhibition of the enzymatic activity of cholinesterase (in %), in relation to increasing doses of neostygmin in the serum.

Figure 3:
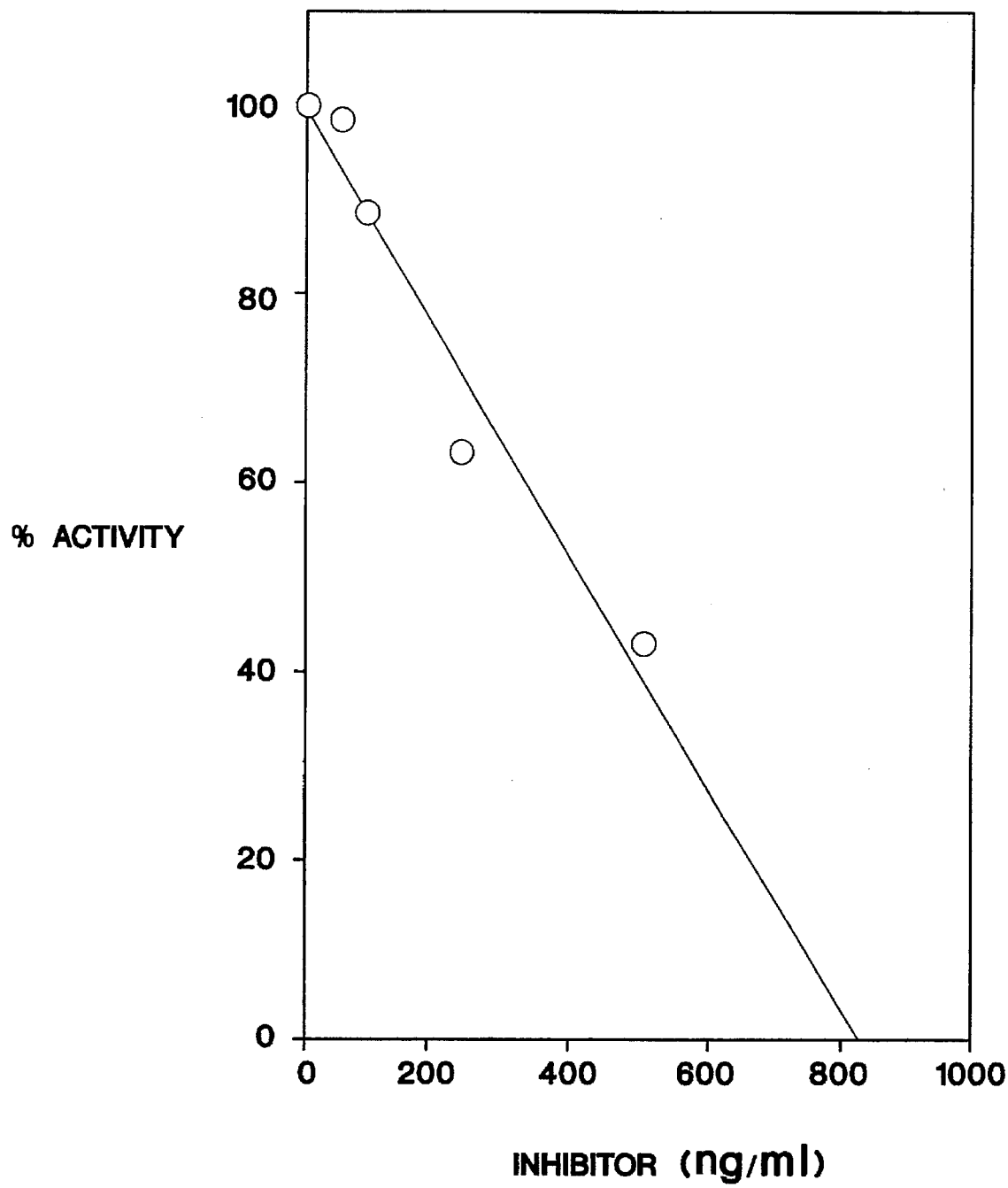

FIG. 3 represents the inhibition of the enzymatic activity of cholinesterase (in %), in relation to increasing doses of eserin in the serum.

EXAMPLE I

Stabilization of acetylcholinesterase (AchE) gelatin and trehalose

Acetylcholinesterase, extracted from torpedo fish and purified by affinity chromatography according to the method of Hirt (Photoaffinity labelling of cholinesterases. Ehret-Sabatier at al. J. Biochem 1992, 203, 475–481), was solubilized in carbonate buffer 0.05 M at pH 9.6 at a concentration of 2 mg/ml and used at 100 µl/ml for the sensitization of wells of microtitration plates. After a night of incubation at 4° C., the wells were rinsed and thereafter subjected to the following analysis:

1. Control (nothing added)
2. Rinsing of the wells with buffered water (0.05 M phosphate pH 7,00) containing 15% trehalose.
3. Covering of the wells with buffered water (0.05 M phosphate pH 7,00) containing 5% gelatin (240 bloom), followed by the elimination of the gelatin without rinsing
4. Covering of the wells with buffered water (0.05 M phosphate pH 7,00) containing 5% gelatin (240 bloom) and 15% trehalose, followed by an elimination of the gelatin witout rinsing.

The gelatin was solubilized by heating at 47° C., then cooling down to 37° C. before dispensing in the wells. The wells of the microtitration plates handled in this way were placed at 4° C., 37° C. and 50° C. during 7 days in a dry incubator, then analyzed for the remaining enzymatic activity, according to Ellman's method. Results are given in adsorbances read at 412 nm (table I).

TABLE I

Residual enzymatic activity after storage of AchE-sensitized wells at different temperatures during 7 days.

|   | 4° C. | 37° C. | 50° C. |
|---|---|---|---|
| 1 Control | 1,72 | 0,42 | 0,05 |
| 2 Trehalose | 1.88 | 0.97 | 0.12 |
| 3 Gelatin | 1.67 | 1.04 | 0.56 |
| 4 Gel. + Trehalose. | 1.79 | 1.82 | 1.71 |

One sees the extraordinary improvement in the stability of the enzyme when the two stabilizing factors are associated, gelatin film and sugar, acting in synergy.

EXAMPLE II

Determination of the concentration of trehalose included in a protecting film, necessary and sufficient to stabilize the enzyme peroxidase Horseradish peroxidase (0.2 mg/ml) was used to sensitize the wells of microtitration plates, following the method described in example I. After sensitization during one night at 4° C., the wells were covered either with a warm solution (47° C. for the solubilisation, 37° C. for the pouring into the wells) of a 5% gelatin solution or a 5% albumin solution, both containing trehalose in decreasing concentrations starting from a concentration of 8 mg/ml. Triton X100 at a concentration of 0.04% was added to the albumin solution, as a wetting agent. The wells were immediately emptied without rinsing and were thereafter placed at 4° C. and 37° C. duiring 7 days in a dry incubator. The remaining peroxidase activity was measured by addition to the wells of 100 µl of a solution of tetramethylbenzidine and hydrogen peroxide in a citrate-phosphate buffer at pH 5.5. The blue coloration obtained changes to yellow with sulfuric acid (100 µl, 0.5 N), added to stop the enzymatic reaction. The results are given in adsorbances read at 450 nm (table II)

TABLE II

| Trehalose | gelatin | | albumin | |
|---|---|---|---|---|
| mg/ml | 4° C. | 37° C. | 4° C. | 37° C. |
| 8,0 | 1.86 | 1.69 | 1.78 | 1.81 |
| 4,0 | 1.78 | 1.74 | 1.79 | 1.73 |
| 2,0 | 1.82 | 1.69 | 1.84 | 1.69 |
| 1,0 | 1.42 | 0.97 | 1.78 | 1.74 |
| 0,5 | 1.13 | 0.48 | 1.67 | 1.43 |
| 0 | 0.97 | 0.36 | 1.37 | 0.52 |

The protection resulting when trehalose was incorporated in the protecting film of polymer is about the same for albumin and gelatin, with perhaps a slight advantage to albumin probably because, contrary to gelatin, this proteinic film does not melt at 37° C. Two percent trehalose, included in the gelifying film, appear sufficient and necessary to stabilize the dry enzyme immobilized on the solid phase.

EXAMPLE 3

Determination of the concentration of trehalose included in a protecting film, necessary and sufficient to stabilize a cholinesterase enzyme A more detailed analysis of the concentration in gelatin and trehalose necessary to obtain an optimal protection of acetylcholinesterase of torpedo fish immobilized dry within the wells of a microtitration plate, is given in table III.

Acetylcholinesterase (AchE) from torpedo fish was fixed into the wells of a microtitration plate according to the method described in example 1. After washing, the wells were immerged during 12 hours at 4° C. in solutions of trehalose, in the presence of 0.5% gelatin. The wells were thereafter emptied and the enzymatic activity of acetylcholinesterase was measured following the method given in example 1. The wells were thereafter maintained at 4° C., room temperature, 37° C. and 50° C. during several days. The residual enzymatic activity was measured after 10 days and 31 days of storage at these temperatures.

The unprotected enzyme, dried into the wells of a microtitration plate, is destroyed after 10 days of storage at 4° C. ( table III). Increasing concentrations of trehalose protect the enzymatic activity but, even with 15% trehalose, 27% of the activity is lost after 10 days storage at 4° C.

Gelatin alone protects the enzymatic activity at room temperature (TA=ambient temperature) and 4° C. but not at 37° C. (measured after 10 days of storage) and very partially after 31 days of storage at 50° C. A concentration of 5% trehalose solubilized in gelatin gives a good protection. One should note that the protection is better at 50° C. than 37° C., probably because the gelatin layer dries immediately at 50° C. in a dry incubator but melts at 37° C. This phenomenon was not systematically observed and is related to the thickness of the gelatin layer, variable with length and temperature adopted for the coating.

TABLE III

| | STABILITY: % residual activity | | | | | | | |
|---|---|---|---|---|---|---|---|---|
| | Day 10 | | | | Day 31 | | | |
| Protection | 4° C. | T.A. | 37° C. | 50° C. | 4° C. | T.A. | 37° C. | 50° C. |
| 0% gelatin | | | | | | | | |
| Trehalose 0% | 0 | 0 | 0 | 0 | | | | |
| 2% | 27 | 22 | 0 | 17 | | | | |
| 5% | 48 | 29 | 8 | 35 | | | | |
| 10% | 69 | 72 | 26 | 44 | | | | |
| 15% | 73 | 76 | 43 | 65 | | | | |
| 0,5% gelatin | | | | | | | | |
| Trehalose 0% | 100 | 100 | 0 | — | 100 | 100 | 0 | 43 |
| 2% | 100 | 100 | 72 | 100 | 100 | 100 | 21 | 100 |
| 5% | 100 | 100 | 100 | 100 | 100 | 100 | 70 | 100 |
| 10% | 100 | 100 | 100 | 100 | 100 | 100 | 69 | 100 |
| 15% | 100 | 100 | 100 | 100 | 100 | 100 | 67 | 100 |

EXAMPLE 4

Stability of two different acetylcholinesterases (AchE) in the presence of albumin and gelatin Acetylcholinesterases (AchE) have different origins (animal species) and are found in different organs. An analysis of the stability of AchE of conger and torpedo fish, in the presence of albumin, albumin plus trehalose and gelatin plus trehalose, shows that these AchE are not equally resistant (table IV). The sensitization of the wells of microtitration plates and the subsequent enzymatic analyses were done according to the protocols described in example 1.

Albumin plus trehalose does not protect the enzyme from either source as well as gelatin plus trehalose (see storage during 50 days at 50° C.) and the effect of the absence of trehalose is more apparent with torpedo AchE: see day 50, 50° C., albumin alone protecting torpedo fish AchE (29% residual activity) versus; AchE of conger (60% residual activity).

EXAMPLE 5

Protection of the AchE enzymatic activity against pH extremes and against cyclohexane Water is normally not buffered and has a pH around 5.5, due to dissolved $CO_2$. Water, analysed without particular caution for the presence of pesticides, may present extremes of pH which may influence the enzymatic activity of acetylcholinesterase, whose optimum is around 7.2. Also, pesticides are normally dissolved in cyclohexane, which may influence the reaction.

The enzymatic activity of the AchE of torpedo fish immobilized in the wells of microtitration plates was verified after exposition during 18 hours at 4° C. to water where the pH was varied by buffers (phosphate, acetate and carbonate) 0.005 M. Also, an analysis was done after incubation of the sensitized wells during 18 hours at 4° C. with cyclohexane. We see in table V that gelatin plus trehalose give excellent protection between pH 5 and 8.2. The activity of the protected enzyme is maintained despite a contact with cyclohexane.

TABLE IV

| | | STABILITY OF TWO DIFFERENT AchE: % of residual activity | | | | | |
|---|---|---|---|---|---|---|---|
| | | ALBUMIN 5% Trehalose 0% | | ALBUMIN 5% Trehalose 5% | | GELATIN 0,5% Trehalose 5% | |
| DAYS | TEMP. | conger | torpedo | conger | torpedo | conger | torpedo |
| 0 | | 100 | 100 | 100 | 100 | 100 | 100 |
| 6 | 37° C. | 100 | 91 | 100 | 100 | 100 | 100 |
| | 50° C. | 96 | 81 | 100 | 100 | 100 | 100 |
| 14 | 37° C. | 100 | 88 | 100 | 100 | 100 | 100 |
| | 50° C. | 88 | 75 | 100 | 100 | 100 | 100 |
| 30 | 37° C. | 100 | 89 | 100 | 100 | 100 | 100 |
| | 50° C. | 88 | 46 | 100 | 100 | 100 | 100 |
| 50 | 37° C. | 86 | 63 | 100 | 100 | 100 | 100 |
| | 50° C. | 60 | 29 | 96 | 90 | 100 | 100 |

TABLE V

| | Relative activity, in percentage | |
|---|---|---|
| | Unprotected | 0.5% gelatine 5% trehalose |
| pH 3 | 07 | 08 |
| 4 | 39 | 80 |
| 5 | 40 | 100 |
| 6 | 44 | 100 |
| 7.2 | 100 | 100 |
| 8.2 | 100 | 100 |
| 9.5 | 13 | 40 |
| 11 | 02 | 02 |
| Cyclohexane | 38 | 100 |

EXAMPLE 6

Stability of conger AchE insolubilized on glas

Acetylcholinesterase of conger was used to sensitize glas tubes. The advantage of sensitization in tubes instead of microtitration wells is the increase of the sensitized surface which, in turn, allows a potential increase in sensitivity of the measures done. Two millilitres of a solution of enzyme were used per tube for the sensitization, according to the protocol described in example 1. After sensitization, the immobilized enzyme was protected by introduction into the tubes of 2 ml of a solution 0.2% in gelatin containing 5% trehalose. After two hours at 4° C., the tubes were emptied and stored during 4 days at different temperatures, before analysis of the residual enzymatic activity, according to the protocol described in example 1. Table VI gives the results of this analysis: the protection achieved with this concentration of gelatin containing this concentration of trehalose is significant, without however attaining the efficacy observed at the same concentrations of protecting agents applied to the sensitized wells of microtitration plates.

TABLE VI

| | | % of residual enzymatic activity | |
|---|---|---|---|
| | | not protected | protected |
| Time 0 | | 100 | — |
| Time 4 days | | | |
| | 4° C. | 19 | 97 |
| | TA | 13 | 61 |
| | 37° C. | 10 | 81 |
| | 50° C. | 8 | 81 |

EXAMPLE 7

Analysis of a pesticide inhibitor of acetylcholinesterase, dissolved in water

The analysis of a common pesticide, Naled, solubilized in water at concentrations of 10, 5, 2.5, 1 and 0 µg/litre, was done with conger AchE in microtitration wells, protected by trehalose and various concentrations of gelatin, albumin, albumin plus gelatin, according to the methods described supra.

The results (table VII) obtained by following the analysis protocols described in example 1, show that the sensitivity of the test (wherein reduction in residual activity of the enzyme is a function of interaction with the pesticide) increases with decreasing concentrations of the polymers, the least satisfying sensitivity being observed with a mixture of gelatin and albumin. In the test, the greatest sensitivity was obtained with 0.1% gelatin.

TABLE VII

| PERCENTAGE OF RESIDUAL ACTIVITY | | | | | |
|---|---|---|---|---|---|
| | NALED (mg/litre) | | | | |
| Protection: 5% trehalose plus: | 10 | 5 | 2 | 1 | 0 |
| 0,1% gelatin | 30 | 50 | 73 | 78 | 100 |
| 0,2% gelatin | 29 | 60 | 80 | 83 | 100 |
| 0,4% gelatin | 36 | 57 | 81 | 88 | 100 |
| 1% albumin | 50 | 67 | 82 | 88 | 100 |
| 2% albumin | 58 | 83 | 82 | 88 | 100 |
| 4% albumin | 69 | 85 | 94 | 96 | 100 |
| 1% albumin plus | | | | | |
| 0,1% gelatin | 52 | 100 | 100 | 100 | 100 |
| 0,2% gelatin | 68 | 99 | 100 | 100 | 100 |

EXAMPLE 8

Analysis of 5 pesticides dissolved in water

Naled, Paraoxon, Dichlorvos, Carbofuran and Carbaryl were analysed at different concentrations in the; wells of microtitration plates sensitized with torpedo fish AchE according to the described method, protected by gelatin-trehalose and used as described in example 1. One sees in table VIII that the sensitivity is not identical for all pesticides: the test is most sensitive for Naled and for Carbofuran, followed closely by Paraoxon. Dichlorvos and Carbaryl are detected with 100 times less sensitivity

TABLE VIII

| Pesticides | % of Residual activity | | | | |
|---|---|---|---|---|---|
| (µg/litre) | Paraoxon | Naled | Dichlorvos | Carbofuran | Carbaryl |
| 1000 | 0 | 0 | 3 | 14 | 18 |
| 100 | 0 | 0 | 49 | 18 | 44 |
| 50 | 0 | 0 | 60 | 20 | 61 |
| 10 | 40 | 11 | 80 | 35 | 80 |
| 01 | 80 | 73 | — | 73 | — |

EXAMPLE 9

Analysis of pesticides in salads

Naled and Carbaryl were diluted at various concentrations in salad extracts. The analysis of the presence of these inhibitors was done following the protocol described in example 1. One sees (table IX) that the sensitivity of the test is similar to that obtained when pesticides are analysed in water.

TABLE IX

| Pesticides | % relative activity | |
|---|---|---|
| (µg/litre) | NALED | CARBARYL |
| 1000 | 3 | 28 |
| 500 | — | 26 |
| 100 | 9 | 51 |
| 50 | 20 | 61 |
| 10 | 63 | 80 |
| 01 | 90 | — |

EXAMPLE 10

Analysis of a drug (pyridostygmin) in serum

Pyridostygmin is a drug used for the treatment of myastheny. Its determination in the serum of patients under treatment is necessary when maximal and subliminary doses are given.

The serum of a healthy subject was spiked with increasing concentrations of pyridostygmin and thereafter analysed for the enzymatic activity of acetylcholinesterase, following the protocol already outlined in former examples. One sees in graph 1 that the detection Of the inhibitor of AchE goes down to 1 to 2 μg/ml of this drug in serum.

EXAMPLE 11

Analysis of a drug (neostygmin) in serum

Neostygmin is a drug used for the treatment of myastheny. Its determination in the serum of patients under treatment is necessary when maximal and subliminary doses are given.

The serum of a healthy subject was spiked with increasing concentrations of neostygmin and thereafter analysed for the enzymatic activity of acetylcholinesterase, following the protocol already outlined in former examples. One sees in graph 2 that the detection of this inhibitor of AchE goes down to 50 ng/ml of this drug in serum.

EXAMPLE 12

Analysis of a drug (eserin) in serum

Eserin is a drug used in the treatment of Alzheimer disease. Its determination in the serum of patients under treatment is necessary when maximal and subliminary doses are given.

A serum of a healthy subject was spiked with increasing concentrations of eserin and thereafter analysed for the enzymatic activity of acetylcholinesterase, following the protocol already outlined in former examples. One sees in graph 3 that the detection of this inhibitor of AchE goes down to 100 ng/ml of this drug in serum.

What is claimed is:

1. A stabilized immobilized acetylcholinesterase having biological activity comprising a solid support having a biologically effective amount of acetylcholinesterase immobilized thereon, and said support with said acetylcholinesterase immobilized thereon having a covering of a protective film comprised of gelatin or albumin containing dispersed therein trehalose, whereby said acetylcholinesterase immboilized on said support exhibits substantially improved resistance to degradation.

2. The stabilized immobilized acetylcholinesterase of claim 1 which is substantially moisture free.

3. The stabilized immobilized acetylcholinesterase of claim 1 which is in tubular form.

4. A process for producing a stabilized immobilized acetylcholinesterase having biological activity which comprises immobilizing on a solid support a biologically effective amount of acetylcholinesterase, covering said solid support with said acetylcholinesterase immobilized thereon with a layer of a gel-forming solution of gelatin or albumin in an evaporable solvent which contains trehalose dissolved therein, and evaporating from the covered support the solvent of said gel-forming solution to leave a covering over said support of a protective film of gel comprising said gelatin or albumin having trehalose dispersed therein.

* * * * *